(12) United States Patent
Valentine et al.

(10) Patent No.: US 11,622,768 B2
(45) Date of Patent: Apr. 11, 2023

(54) METHODS AND STRUCTURE FOR CONFIRMING PROPER ASSEMBLY OF POWERED SURGICAL STAPLING SYSTEMS

(71) Applicant: Covidien LP, Mansfield, MA (US)

(72) Inventors: David E. Valentine, Hamden, CT (US); Charles R. Kollar, West Hartford, CT (US); Alexander Hart, Tolland, CT (US); Drew R. Seils, Guilford, CT (US); Stephen R. Paul, East Hartford, CT (US); Joseph T. Eisinger, Northford, CT (US)

(73) Assignee: COVIDIEN LP, Mansfield, MA (US)

( * ) Notice: Subject to any disclaimer, the term of this patent is extended or adjusted under 35 U.S.C. 154(b) by 114 days.

(21) Appl. No.: 17/346,496

(22) Filed: Jun. 14, 2021

(65) Prior Publication Data

US 2022/0008077 A1    Jan. 13, 2022

Related U.S. Application Data (60) Provisional application No. 63/050,994, filed on Jul. 13, 2020.

(51) Int. Cl.
*A61B 17/115* (2006.01)
*G16H 40/63* (2018.01)
(Continued)

(52) U.S. Cl.
CPC ...... *A61B 17/1155* (2013.01); *A61B 17/3403* (2013.01); *G16H 40/63* (2018.01);
(Continued)

(58) Field of Classification Search
CPC .............................. A61B 34/35; G16H 40/63
See application file for complete search history.

(56) References Cited

U.S. PATENT DOCUMENTS

| 37,165 A | 12/1862 | Gary |
|---|---|---|
| 3,209,754 A | 10/1965 | Brown |
| (Continued) | | |

FOREIGN PATENT DOCUMENTS

| CN | 101683284 A | 3/2010 |
|---|---|---|
| CN | 102648864 A | 8/2012 |
| (Continued) | | |

OTHER PUBLICATIONS

Detemple, P., "Microtechnology in Modem Health Care", Med Device Technol. 9(9):18-25 (1998).

(Continued)

*Primary Examiner* — Nathaniel C Chukwurah
(74) *Attorney, Agent, or Firm* — Carter, DeLuca & Farrell LLP (57) ABSTRACT

A surgical stapling system includes an adapter assembly, a trocar assembly attachable to the adapter assembly, a processor, and memory. The memory includes instructions executable by the processor to cause the trocar assembly to move relative to the adapter assembly and determine whether the trocar assembly is properly attached to the adapter assembly. Such determination is based on an amount of force applied between the trocar assembly and the adapter assembly, an amount of current detected in the surgical stapling system, or an amount of time the trocar assembly moves relative to the adapter assembly without an indication that the amount of force is within a predetermined range.

19 Claims, 7 Drawing Sheets

(51) Int. Cl.
*A61B 17/34* (2006.01)
*A61B 17/00* (2006.01)
(52) U.S. Cl.
CPC .............. A61B 2017/00022 (2013.01); A61B 2017/3454 (2013.01); A61B 2562/0261 (2013.01)

(56) References Cited

U.S. PATENT DOCUMENTS

| | | |
|---|---|---|
| 3,273,562 A | 9/1966 | Brown |
| 3,499,591 A | 3/1970 | Green |
| 3,528,693 A | 9/1970 | Pearson et al. |
| 3,744,495 A | 7/1973 | Johnson |
| 3,862,631 A | 1/1975 | Austin |
| 3,949,924 A | 4/1976 | Green |
| 4,060,089 A | 11/1977 | Noiles |
| 4,204,623 A | 5/1980 | Green |
| 4,217,902 A | 8/1980 | March |
| 4,263,903 A | 4/1981 | Griggs |
| 4,275,813 A | 6/1981 | Noiles |
| 4,331,277 A | 5/1982 | Green |
| 4,428,376 A | 1/1984 | Mericle |
| 4,429,695 A | 2/1984 | Green |
| 4,444,181 A | 4/1984 | Wevers et al. |
| 4,454,875 A | 6/1984 | Pratt et al. |
| 4,456,006 A | 6/1984 | Wevers et al. |
| 4,485,816 A | 12/1984 | Krumme |
| 4,485,817 A | 12/1984 | Swiggett |
| 4,488,523 A | 12/1984 | Shichman |
| 4,508,253 A | 4/1985 | Green |
| 4,508,523 A | 4/1985 | Leu |
| 4,522,206 A | 6/1985 | Whipple et al. |
| 4,534,350 A | 8/1985 | Golden et al. |
| 4,535,772 A | 8/1985 | Sheehan |
| 4,566,620 A | 1/1986 | Green et al. |
| 4,570,623 A | 2/1986 | Ellison et al. |
| 4,606,343 A | 8/1986 | Conta et al. |
| 4,606,344 A | 8/1986 | Di Giovanni |
| 4,610,383 A | 9/1986 | Rothfuss et al. |
| 4,612,923 A | 9/1986 | Kronenthal |
| 4,612,933 A | 9/1986 | Brinkerhoff et al. |
| D286,442 S | 10/1986 | Korthoff et al. |
| 4,627,437 A | 12/1986 | Bedi et al. |
| 4,635,637 A | 1/1987 | Schreiber |
| 4,662,371 A | 5/1987 | Whipple et al. |
| 4,671,280 A | 6/1987 | Dorband et al. |
| 4,705,038 A | 11/1987 | Sjostrom et al. |
| 4,712,550 A | 12/1987 | Sinnett |
| 4,719,917 A | 1/1988 | Barrows et al. |
| 4,724,839 A | 2/1988 | Bedi et al. |
| 4,731,058 A | 3/1988 | Doan |
| 4,805,617 A | 2/1989 | Bedi et al. |
| 4,807,628 A | 2/1989 | Peters et al. |
| 4,852,558 A | 8/1989 | Outerbridge |
| 4,913,144 A | 4/1990 | Del Medico |
| 4,960,420 A | 10/1990 | Goble et al. |
| 4,962,877 A | 10/1990 | Hervas |
| 4,990,153 A | 2/1991 | Richards |
| 4,994,073 A | 2/1991 | Green |
| 4,995,877 A | 2/1991 | Ams et al. |
| 5,040,715 A | 8/1991 | Green et al. |
| 5,065,929 A | 11/1991 | Schulze et al. |
| 5,089,009 A | 2/1992 | Green |
| 5,108,422 A | 4/1992 | Green et al. |
| 5,114,399 A | 5/1992 | Kovalcheck |
| 5,129,570 A | 7/1992 | Schulze et al. |
| 5,143,453 A | 9/1992 | Weynant |
| 5,203,864 A | 4/1993 | Phillips |
| 5,207,697 A | 5/1993 | Carusillo et al. |
| 5,209,756 A | 5/1993 | Seedhom et al. |
| 5,246,443 A | 9/1993 | Mai |
| 5,258,008 A | 11/1993 | Wilk |
| 5,271,543 A | 12/1993 | Grant et al. |
| RE34,519 E | 1/1994 | Fox et al. |
| 5,282,829 A | 2/1994 | Hermes |
| 5,300,081 A | 4/1994 | Young et al. |
| 5,307,976 A | 5/1994 | Olson et al. |
| 5,312,023 A | 5/1994 | Green et al. |
| 5,312,024 A | 5/1994 | Grant et al. |
| 5,313,935 A | 5/1994 | Kortenbach et al. |
| 5,318,221 A | 6/1994 | Green et al. |
| 5,326,013 A | 7/1994 | Green et al. |
| 5,330,486 A | 7/1994 | Wilk |
| 5,332,142 A | 7/1994 | Robinson et al. |
| 5,342,376 A | 8/1994 | Ruff |
| 5,350,355 A | 9/1994 | Sklar |
| 5,356,064 A | 10/1994 | Green et al. |
| 5,359,993 A | 11/1994 | Slater et al. |
| 5,364,001 A | 11/1994 | Bryan |
| 5,381,943 A | 1/1995 | Allen et al. |
| 5,383,874 A | 1/1995 | Jackson et al. |
| 5,383,880 A | 1/1995 | Hooven |
| 5,389,098 A | 2/1995 | Tsuruta et al. |
| 5,391,166 A | 2/1995 | Eggers |
| 5,395,030 A | 3/1995 | Kuramoto et al. |
| 5,395,033 A | 3/1995 | Byrne et al. |
| 5,400,267 A | 3/1995 | Denen et al. |
| 5,403,312 A | 4/1995 | Yates et al. |
| 5,405,344 A | 4/1995 | Williamson et al. |
| 5,411,508 A | 5/1995 | Bessler et al. |
| 5,413,267 A | 5/1995 | Solyntjes et al. |
| 5,431,323 A | 7/1995 | Smith et al. |
| 5,464,144 A | 11/1995 | Guy et al. |
| 5,467,911 A | 11/1995 | Tsuruta et al. |
| 5,478,344 A | 12/1995 | Stone et al. |
| 5,482,100 A | 1/1996 | Kuhar |
| 5,485,947 A | 1/1996 | Olson et al. |
| 5,487,499 A | 1/1996 | Sorrentino et al. |
| 5,497,933 A | 3/1996 | DeFonzo et al. |
| 5,500,000 A | 3/1996 | Feagin et al. |
| 5,503,320 A | 4/1996 | Webster et al. |
| 5,507,743 A | 4/1996 | Edwards et al. |
| 5,518,163 A | 5/1996 | Hooven |
| 5,518,164 A | 5/1996 | Hooven |
| 5,526,822 A | 6/1996 | Burbank et al. |
| 5,529,235 A | 6/1996 | Boiarski et al. |
| 5,531,744 A | 7/1996 | Nardella et al. |
| 5,533,661 A | 7/1996 | Main et al. |
| 5,535,934 A | 7/1996 | Boiarski et al. |
| 5,535,937 A | 7/1996 | Boiarski et al. |
| 5,558,671 A | 9/1996 | Yates |
| 5,560,532 A | 10/1996 | DeFonzo et al. |
| 5,562,239 A | 10/1996 | Boiarski et al. |
| 5,571,285 A | 11/1996 | Chow et al. |
| 5,575,799 A | 11/1996 | Bolanos et al. |
| 5,582,611 A | 12/1996 | Tsuruta et al. |
| 5,584,835 A | 12/1996 | Greenfield |
| 5,601,224 A | 2/1997 | Bishop et al. |
| 5,601,558 A | 2/1997 | Torrie et al. |
| 5,607,095 A | 3/1997 | Smith et al. |
| 5,609,285 A | 3/1997 | Grant et al. |
| 5,609,560 A | 3/1997 | Ichikawa et al. |
| 5,624,452 A | 4/1997 | Yates |
| 5,632,433 A | 5/1997 | Grant et al. |
| 5,634,926 A | 6/1997 | Jobe |
| 5,642,848 A | 7/1997 | Ludwig et al. |
| 5,653,374 A | 8/1997 | Young et al. |
| 5,658,300 A | 8/1997 | Bito et al. |
| 5,658,312 A | 8/1997 | Green et al. |
| 5,662,662 A | 9/1997 | Bishop et al. |
| 5,665,085 A | 9/1997 | Nardella |
| 5,667,513 A | 9/1997 | Torrie et al. |
| 5,667,517 A | 9/1997 | Hooven |
| 5,667,527 A | 9/1997 | Cook |
| 5,669,544 A | 9/1997 | Schulze et al. |
| 5,673,841 A | 10/1997 | Schulze et al. |
| 5,676,674 A | 10/1997 | Bolanos et al. |
| 5,680,981 A | 10/1997 | Mililli et al. |
| 5,680,982 A | 10/1997 | Schulze et al. |
| 5,690,675 A | 11/1997 | Sawyer et al. |
| 5,692,668 A | 12/1997 | Schulze et al. |
| 5,695,506 A | 12/1997 | Pike et al. |
| 5,695,524 A | 12/1997 | Kelley et al. |
| 5,702,447 A | 12/1997 | Walch et al. |

(56) References Cited

U.S. PATENT DOCUMENTS

| | | |
|---|---|---|
| 5,704,534 A | 1/1998 | Huitema et al. |
| 5,713,505 A | 2/1998 | Huitema |
| 5,713,896 A | 2/1998 | Nardella |
| 5,715,987 A | 2/1998 | Kelley et al. |
| 5,716,366 A | 2/1998 | Yates |
| 5,720,753 A | 2/1998 | Sander et al. |
| 5,725,529 A | 3/1998 | Nicholson et al. |
| 5,728,110 A | 3/1998 | Vidal et al. |
| 5,728,116 A | 3/1998 | Rosenman |
| 5,730,757 A | 3/1998 | Benetti et al. |
| 5,735,848 A | 4/1998 | Yates et al. |
| 5,738,474 A | 4/1998 | Blewett |
| 5,755,726 A | 5/1998 | Pratt et al. |
| 5,759,171 A | 6/1998 | Coelho et al. |
| 5,779,130 A | 7/1998 | Alesi et al. |
| 5,782,397 A | 7/1998 | Koukline |
| 5,785,713 A | 7/1998 | Jobe |
| 5,788,698 A | 8/1998 | Savornin |
| 5,810,811 A | 9/1998 | Yates et al. |
| 5,823,066 A | 10/1998 | Huitema et al. |
| 5,829,662 A | 11/1998 | Allen et al. |
| 5,830,121 A | 11/1998 | Enomoto et al. |
| 5,849,023 A | 12/1998 | Mericle |
| 5,849,028 A | 12/1998 | Chen |
| 5,855,311 A | 1/1999 | Hamblin et al. |
| 5,861,005 A | 1/1999 | Kontos |
| 5,865,361 A | 2/1999 | Milliman et al. |
| 5,876,401 A | 3/1999 | Schulze et al. |
| 5,891,156 A | 4/1999 | Gessner et al. |
| 5,893,813 A | 4/1999 | Yamamoto |
| 5,895,396 A | 4/1999 | Day et al. |
| 5,906,607 A | 5/1999 | Taylor et al. |
| 5,911,721 A | 6/1999 | Nicholson et al. |
| 5,918,791 A | 7/1999 | Sorrentino et al. |
| 5,928,222 A | 7/1999 | Kleinerman |
| 5,944,717 A | 8/1999 | Lee et al. |
| 5,944,736 A | 8/1999 | Taylor et al. |
| 5,954,259 A | 9/1999 | Viola et al. |
| 5,961,521 A | 10/1999 | Roger |
| 5,964,394 A | 10/1999 | Robertson |
| 5,968,044 A | 10/1999 | Nicholson et al. |
| 5,976,171 A | 11/1999 | Taylor |
| 5,980,518 A | 11/1999 | Carr et al. |
| 5,980,548 A | 11/1999 | Evans et al. |
| 5,991,355 A | 11/1999 | Dahlke |
| 5,991,650 A | 11/1999 | Swanson et al. |
| 5,992,724 A | 11/1999 | Snyder |
| 5,997,552 A | 12/1999 | Person et al. |
| 6,004,335 A | 12/1999 | Vaitekunas et al. |
| 6,007,550 A | 12/1999 | Wang et al. |
| 6,010,054 A | 1/2000 | Johnson et al. |
| 6,013,077 A | 1/2000 | Harwin |
| 6,015,417 A | 1/2000 | Reynolds, Jr. |
| 6,017,354 A | 1/2000 | Culp et al. |
| 6,030,410 A | 2/2000 | Zurbrugg |
| 6,032,849 A | 3/2000 | Mastri et al. |
| 6,039,731 A | 3/2000 | Taylor et al. |
| 6,051,007 A | 4/2000 | Hogendijk et al. |
| 6,063,078 A | 5/2000 | Wittkampf |
| 6,063,095 A | 5/2000 | Wang et al. |
| 6,077,246 A | 6/2000 | Kullas et al. |
| 6,079,606 A | 6/2000 | Milliman et al. |
| 6,080,150 A | 6/2000 | Gough |
| 6,083,242 A | 7/2000 | Cook |
| 6,090,123 A | 7/2000 | Culp et al. |
| 6,092,422 A | 7/2000 | Binnig et al. |
| 6,109,500 A | 8/2000 | Alli et al. |
| 6,113,592 A | 9/2000 | Taylor |
| 6,123,702 A | 9/2000 | Swanson et al. |
| H1904 H | 10/2000 | Yates et al. |
| 6,126,058 A | 10/2000 | Adams et al. |
| 6,126,651 A | 10/2000 | Mayer |
| 6,127,811 A | 10/2000 | Shenoy et al. |
| 6,132,425 A | 10/2000 | Gough |
| 6,165,169 A | 12/2000 | Panescu et al. |
| 6,166,538 A | 12/2000 | D'Alfonso |
| 6,179,840 B1 | 1/2001 | Bowman |
| 6,187,009 B1 | 2/2001 | Herzog et al. |
| 6,187,019 B1 | 2/2001 | Stefanchik et al. |
| 6,190,401 B1 | 2/2001 | Green et al. |
| 6,193,501 B1 | 2/2001 | Masel et al. |
| 6,202,914 B1 | 3/2001 | Geiste et al. |
| 6,217,573 B1 | 4/2001 | Webster |
| 6,228,534 B1 | 5/2001 | Takeuchi et al. |
| 6,231,565 B1 | 5/2001 | Tovey et al. |
| 6,236,874 B1 | 5/2001 | Devlin et al. |
| 6,237,604 B1 | 5/2001 | Burnside et al. |
| 6,241,139 B1 | 6/2001 | Milliman et al. |
| 6,245,065 B1 | 6/2001 | Panescu et al. |
| 6,248,117 B1 | 6/2001 | Blatter |
| 6,250,532 B1 | 6/2001 | Green et al. |
| 6,258,111 B1 | 7/2001 | Ross et al. |
| 6,264,086 B1 | 7/2001 | McGuckin, Jr. |
| 6,264,087 B1 | 7/2001 | Whitman |
| 6,264,653 B1 | 7/2001 | Falwell |
| 6,281,471 B1 | 8/2001 | Smart |
| 6,288,534 B1 | 9/2001 | Starkweather et al. |
| 6,290,701 B1 | 9/2001 | Enayati |
| 6,293,943 B1 | 9/2001 | Panescu et al. |
| 6,295,330 B1 | 9/2001 | Skog et al. |
| 6,315,184 B1 | 11/2001 | Whitman |
| 6,329,778 B1 | 12/2001 | Culp et al. |
| 6,330,965 B1 | 12/2001 | Milliman et al. |
| 6,346,104 B2 | 2/2002 | Daly et al. |
| 6,355,066 B1 | 3/2002 | Kim |
| 6,364,884 B1 | 4/2002 | Bowman et al. |
| 6,387,092 B1 | 5/2002 | Burnside et al. |
| 6,388,240 B2 | 5/2002 | Schulz et al. |
| 6,402,766 B2 | 6/2002 | Bowman et al. |
| H2037 H | 7/2002 | Yates et al. |
| 6,412,279 B1 | 7/2002 | Coleman et al. |
| 6,425,903 B1 | 7/2002 | Voegele |
| 6,436,097 B1 | 8/2002 | Nardella |
| 6,436,107 B1 | 8/2002 | Wang et al. |
| 6,436,110 B2 | 8/2002 | Bowman et al. |
| 6,443,973 B1 | 9/2002 | Whitman |
| 6,447,517 B1 | 9/2002 | Bowman |
| 6,461,372 B1 | 10/2002 | Jensen et al. |
| 6,478,210 B2 | 11/2002 | Adams et al. |
| 6,497,707 B1 | 12/2002 | Bowman et al. |
| 6,505,768 B2 | 1/2003 | Whitman |
| 6,515,273 B2 | 2/2003 | Al-Ali |
| 6,524,316 B1 | 2/2003 | Nicholson et al. |
| 6,533,157 B1 | 3/2003 | Whitman |
| 6,540,751 B2 | 4/2003 | Enayati |
| 6,544,273 B1 | 4/2003 | Harari et al. |
| 6,554,852 B1 | 4/2003 | Oberlander |
| 6,562,071 B2 | 5/2003 | Jarvinen |
| 6,578,579 B2 | 6/2003 | Burnside et al. |
| 6,601,748 B1 | 8/2003 | Fung et al. |
| 6,601,749 B2 | 8/2003 | Sullivan et al. |
| 6,602,252 B2 | 8/2003 | Mollenauer |
| 6,611,793 B1 | 8/2003 | Burnside et al. |
| 6,616,821 B2 | 9/2003 | Broadley et al. |
| 6,629,986 B1 | 10/2003 | Ross et al. |
| 6,651,669 B1 | 11/2003 | Burnside |
| 6,656,177 B2 | 12/2003 | Truckai et al. |
| 6,669,073 B2 | 12/2003 | Milliman et al. |
| 6,669,705 B2 | 12/2003 | Westhaver et al. |
| 6,696,008 B2 | 2/2004 | Brandinger |
| 6,698,643 B2 | 3/2004 | Whitman |
| 6,699,177 B1 | 3/2004 | Wang et al. |
| 6,716,233 B1 | 4/2004 | Whitman |
| 6,736,085 B1 | 5/2004 | Esnouf |
| 6,792,390 B1 | 9/2004 | Burnside et al. |
| 6,793,652 B1 | 9/2004 | Whitman et al. |
| 6,817,508 B1 | 11/2004 | Racenet et al. |
| 6,830,174 B2 | 12/2004 | Hillstead et al. |
| 6,843,403 B2 | 1/2005 | Whitman |
| 6,846,307 B2 | 1/2005 | Whitman et al. |
| 6,846,308 B2 | 1/2005 | Whitman et al. |
| 6,846,309 B2 | 1/2005 | Whitman et al. |
| 6,849,071 B2 | 2/2005 | Whitman et al. |
| 6,861,639 B2 | 3/2005 | Al-Ali |

(56) References Cited

U.S. PATENT DOCUMENTS

| | | |
|---|---|---|
| 6,872,214 B2 | 3/2005 | Sonnenschein et al. |
| 6,899,538 B2 | 5/2005 | Matoba |
| 6,900,004 B2 | 5/2005 | Satake |
| 6,905,057 B2 | 6/2005 | Swayze et al. |
| 6,926,636 B2 | 8/2005 | Luper |
| 6,953,139 B2 | 10/2005 | Milliman et al. |
| 6,959,852 B2 | 11/2005 | Shelton, IV et al. |
| 6,964,363 B2 | 11/2005 | Wales et al. |
| 6,979,328 B2 | 12/2005 | Baerveldt et al. |
| 6,981,628 B2 | 1/2006 | Wales |
| 6,981,941 B2 | 1/2006 | Whitman et al. |
| 6,988,649 B2 | 1/2006 | Shelton, IV et al. |
| 7,000,819 B2 | 2/2006 | Swayze et al. |
| 7,032,798 B2 | 4/2006 | Whitman et al. |
| 7,044,353 B2 | 5/2006 | Mastri et al. |
| 7,048,687 B1 | 5/2006 | Reuss et al. |
| 7,055,731 B2 | 6/2006 | Shelton, IV et al. |
| 7,059,508 B2 | 6/2006 | Shelton, IV et al. |
| 7,077,856 B2 | 7/2006 | Whitman |
| 7,083,075 B2 | 8/2006 | Swayze et al. |
| 7,097,089 B2 | 8/2006 | Marczyk |
| 7,111,769 B2 | 9/2006 | Wales et al. |
| 7,118,564 B2 | 10/2006 | Ritchie et al. |
| 7,122,029 B2 | 10/2006 | Koop et al. |
| 7,128,253 B2 | 10/2006 | Mastri et al. |
| 7,128,254 B2 | 10/2006 | Shelton, IV et al. |
| 7,140,528 B2 | 11/2006 | Shelton, IV |
| 7,143,924 B2 | 12/2006 | Scirica et al. |
| 7,143,925 B2 | 12/2006 | Shelton, IV et al. |
| 7,143,926 B2 | 12/2006 | Shelton, IV et al. |
| 7,147,138 B2 | 12/2006 | Shelton, IV |
| 7,186,966 B2 | 3/2007 | Al-Ali |
| 7,193,519 B2 | 3/2007 | Root et al. |
| 7,217,269 B2 | 5/2007 | El-Galley et al. |
| 7,220,232 B2 | 5/2007 | Suorsa et al. |
| 7,240,817 B2 | 7/2007 | Higuchi |
| 7,241,270 B2 | 7/2007 | Horzewski et al. |
| 7,246,734 B2 | 7/2007 | Shelton, IV |
| 7,303,108 B2 | 12/2007 | Shelton, IV |
| 7,328,828 B2 | 2/2008 | Ortiz et al. |
| 7,335,169 B2 | 2/2008 | Thompson et al. |
| 7,364,061 B2 | 4/2008 | Swayze et al. |
| 7,380,695 B2 | 6/2008 | Doll et al. |
| 7,380,696 B2 | 6/2008 | Shelton, IV et al. |
| 7,404,508 B2 | 7/2008 | Smith et al. |
| 7,416,101 B2 | 8/2008 | Shelton, IV et al. |
| 7,419,080 B2 | 9/2008 | Smith et al. |
| 7,422,136 B1 | 9/2008 | Marczyk |
| 7,422,139 B2 | 9/2008 | Shelton, IV et al. |
| 7,431,188 B1 | 10/2008 | Marczyk |
| 7,431,189 B2 | 10/2008 | Shelton, IV et al. |
| 7,434,715 B2 | 10/2008 | Shelton, IV et al. |
| 7,441,684 B2 | 10/2008 | Shelton, IV et al. |
| 7,448,525 B2 | 11/2008 | Shelton, IV et al. |
| 7,461,767 B2 | 12/2008 | Viola et al. |
| 7,464,846 B2 | 12/2008 | Shelton, IV et al. |
| 7,464,847 B2 | 12/2008 | Viola et al. |
| 7,464,849 B2 | 12/2008 | Shelton, IV et al. |
| 7,481,348 B2 | 1/2009 | Marczyk |
| 7,487,899 B2 | 2/2009 | Shelton, IV et al. |
| 7,549,563 B2 | 6/2009 | Mather et al. |
| 7,552,854 B2 | 6/2009 | Wixey et al. |
| 7,556,185 B2 | 7/2009 | Viola |
| 7,568,603 B2 | 8/2009 | Shelton, IV et al. |
| 7,637,409 B2 | 12/2009 | Marczyk |
| 7,641,093 B2 | 1/2010 | Doll et al. |
| 7,644,848 B2 | 1/2010 | Swayze et al. |
| 7,648,055 B2 | 1/2010 | Marczyk |
| 7,670,334 B2 | 3/2010 | Hueil et al. |
| 7,694,809 B2 | 4/2010 | Garbini et al. |
| 7,721,931 B2 | 5/2010 | Shelton, IV et al. |
| 7,740,159 B2 | 6/2010 | Shelton, IV et al. |
| 7,753,248 B2 | 7/2010 | Viola |
| 7,757,925 B2 | 7/2010 | Viola et al. |
| 7,766,207 B2 | 8/2010 | Mather et al. |
| 7,766,210 B2 | 8/2010 | Shelton, IV et al. |
| 7,770,775 B2 | 8/2010 | Shelton, IV et al. |
| 7,784,663 B2 | 8/2010 | Shelton, IV |
| 7,815,090 B2 | 10/2010 | Marczyk |
| 7,823,760 B2 | 11/2010 | Zemlok et al. |
| 7,845,534 B2 | 12/2010 | Viola et al. |
| 7,870,989 B2 | 1/2011 | Viola et al. |
| 7,886,953 B2 | 2/2011 | Schwemberger et al. |
| 7,887,530 B2 | 2/2011 | Zemlok et al. |
| 7,905,897 B2 | 3/2011 | Whitman et al. |
| 7,909,221 B2 | 3/2011 | Viola et al. |
| 7,922,063 B2 | 4/2011 | Zemlok et al. |
| 7,931,660 B2 | 4/2011 | Aranyi et al. |
| 7,950,560 B2 | 5/2011 | Zemlok et al. |
| 7,955,352 B2 | 6/2011 | McEwen et al. |
| 8,006,885 B2 | 8/2011 | Marczyk |
| 8,006,887 B2 | 8/2011 | Marczyk |
| 8,011,551 B2 | 9/2011 | Marczyk et al. |
| 8,020,742 B2 | 9/2011 | Marczyk |
| 8,025,199 B2 | 9/2011 | Whitman et al. |
| 8,038,044 B2 | 10/2011 | Viola |
| 8,052,024 B2 | 11/2011 | Viola et al. |
| 8,066,721 B2 | 11/2011 | Kortenbach et al. |
| 8,074,858 B2 | 12/2011 | Marczyk |
| 8,092,493 B2 | 1/2012 | Marczyk |
| 8,128,645 B2 | 3/2012 | Sonnenschein et al. |
| 8,132,705 B2 | 3/2012 | Viola et al. |
| 8,157,150 B2 | 4/2012 | Viola et al. |
| 8,186,555 B2 | 5/2012 | Shelton, IV et al. |
| 8,201,721 B2 | 6/2012 | Zemlok et al. |
| 8,210,412 B2 | 7/2012 | Marczyk |
| 8,240,536 B2 | 8/2012 | Marczyk |
| 8,240,537 B2 | 8/2012 | Marczyk |
| 8,267,924 B2 | 9/2012 | Zemlok et al. |
| 8,328,823 B2 | 12/2012 | Aranyi et al. |
| 8,348,125 B2 | 1/2013 | Viola et al. |
| 8,685,004 B2 | 4/2014 | Zemlock et al. |
| 9,192,381 B2 | 11/2015 | Marczyk |
| 9,364,222 B2 | 6/2016 | Zemlok et al. |
| 9,370,360 B2 | 6/2016 | Marczyk |
| 9,370,361 B2 | 6/2016 | Viola et al. |
| 9,433,415 B2 | 9/2016 | Marczyk et al. |
| 9,480,492 B2 | 11/2016 | Aranyi et al. |
| 9,585,659 B2 | 3/2017 | Viola et al. |
| 10,492,814 B2 | 12/2019 | Snow et al. |
| 10,722,222 B2 | 7/2020 | Aranyi |
| 2002/0103489 A1 | 8/2002 | Ku |
| 2002/0111641 A1 | 8/2002 | Peterson et al. |
| 2002/0165541 A1 | 11/2002 | Whitman |
| 2003/0090201 A1 | 5/2003 | Peng |
| 2003/0114851 A1 | 6/2003 | Truckai et al. |
| 2003/0120306 A1 | 6/2003 | Burbank et al. |
| 2004/0232201 A1 | 11/2004 | Wenchell et al. |
| 2005/0006429 A1 | 1/2005 | Wales et al. |
| 2005/0010235 A1 | 1/2005 | VanDusseldorp |
| 2005/0131390 A1 | 6/2005 | Heinrich et al. |
| 2005/0139636 A1 | 6/2005 | Schwemberger et al. |
| 2005/0177176 A1 | 8/2005 | Gerbi et al. |
| 2005/0192609 A1 | 9/2005 | Whitman et al. |
| 2005/0247753 A1 | 11/2005 | Kelly et al. |
| 2006/0000867 A1 | 1/2006 | Shelton et al. |
| 2007/0023477 A1 | 2/2007 | Whitman et al. |
| 2007/0029363 A1 | 2/2007 | Popov |
| 2007/0084897 A1 | 4/2007 | Shelton et al. |
| 2007/0102472 A1 | 5/2007 | Shelton |
| 2007/0175949 A1 | 8/2007 | Shelton et al. |
| 2007/0175950 A1 | 8/2007 | Shelton et al. |
| 2007/0175951 A1 | 8/2007 | Shelton et al. |
| 2007/0175955 A1 | 8/2007 | Shelton et al. |
| 2007/0219563 A1 | 9/2007 | Voegele |
| 2008/0029570 A1 | 2/2008 | Shelton et al. |
| 2008/0029573 A1 | 2/2008 | Shelton et al. |
| 2008/0029574 A1 | 2/2008 | Shelton et al. |
| 2008/0029575 A1 | 2/2008 | Shelton et al. |
| 2008/0135600 A1 | 6/2008 | Hiranuma et al. |
| 2008/0169329 A1 | 7/2008 | Shelton et al. |
| 2008/0185419 A1* | 8/2008 | Smith ............... A61B 17/1155 227/179.1 |
| 2008/0197167 A1 | 8/2008 | Viola et al. |

(56) References Cited

U.S. PATENT DOCUMENTS

| | | |
|---|---|---|
| 2008/0255413 A1 | 10/2008 | Zemlok et al. |
| 2008/0255607 A1 | 10/2008 | Zemlok |
| 2009/0018624 A1 | 1/2009 | Levinson et al. |
| 2009/0090201 A1 | 4/2009 | Viola |
| 2009/0090763 A1 | 4/2009 | Zemlok et al. |
| 2010/0200636 A1 | 8/2010 | Zemlok et al. |
| 2010/0312257 A1 | 12/2010 | Aranyi |
| 2010/0320254 A1 | 12/2010 | Zemlok et al. |
| 2011/0034910 A1 | 2/2011 | Ross et al. |
| 2011/0062211 A1 | 3/2011 | Ross et al. |
| 2011/0121049 A1 | 5/2011 | Malinouskas et al. |
| 2011/0168757 A1 | 7/2011 | Viola et al. |
| 2011/0172681 A1 | 7/2011 | Aranyi et al. |
| 2011/0190738 A1 | 8/2011 | Zemlok et al. |
| 2011/0301579 A1 | 12/2011 | Marczyk et al. |
| 2011/0303735 A1 | 12/2011 | Marczyk |
| 2012/0055972 A1 | 3/2012 | Marczyk |
| 2012/0074197 A1 | 3/2012 | Marczyk |
| 2012/0116416 A1 | 5/2012 | Neff et al. |
| 2012/0175400 A1 | 7/2012 | Viola et al. |
| 2012/0193393 A1 | 8/2012 | Viola et al. |
| 2012/0198288 A1 | 8/2012 | Njo et al. |
| 2012/0220989 A1 | 8/2012 | Zemlok et al. |
| 2012/0223121 A1 | 9/2012 | Viola et al. |
| 2012/0241494 A1 | 9/2012 | Marczyk |
| 2012/0277790 A1 | 11/2012 | Zemlok et al. |
| 2012/0298718 A1 | 11/2012 | Marczyk |
| 2012/0298720 A1 | 11/2012 | Marczyk |
| 2015/0157320 A1 | 6/2015 | Zergiebel et al. |
| 2015/0297199 A1 | 10/2015 | Nicholas et al. |
| 2020/0015824 A1 | 1/2020 | Eisinger et al. |
| 2020/0188053 A1 | 6/2020 | Williams et al. |

FOREIGN PATENT DOCUMENTS

| | | | |
|---|---|---|---|
| EP | 0537570 | A2 | 4/1993 |
| EP | 0647431 | A2 | 4/1995 |
| EP | 0738501 | A1 | 10/1996 |
| EP | 0770354 | A1 | 5/1997 |
| EP | 1070487 | A2 | 1/2001 |
| EP | 1201196 | A1 | 5/2002 |
| EP | 1658817 | A1 | 5/2006 |
| EP | 1813203 | A2 | 8/2007 |
| EP | 3632346 | A1 | 4/2020 |
| FR | 2 849 589 | A1 | 7/2004 |
| WO | 9414129 | A1 | 6/1994 |
| WO | 9729694 | A1 | 8/1997 |
| WO | 9740760 | A1 | 11/1997 |
| WO | 9837825 | A1 | 9/1998 |
| WO | 1999/52489 | A1 | 10/1999 |
| WO | 0234140 | A2 | 5/2002 |
| WO | 03026511 | A1 | 4/2003 |
| WO | 03030743 | A2 | 4/2003 |
| WO | 2004032760 | A2 | 4/2004 |
| WO | 2007030753 | A2 | 3/2007 |
| WO | 2007/114868 | A2 | 10/2007 |
| WO | 2007118179 | A2 | 10/2007 |
| WO | 2009039506 | A1 | 3/2009 |
| WO | 2007014355 | A3 | 4/2009 |
| WO | 2009143092 | A1 | 11/2009 |
| WO | 2016025132 | A1 | 2/2016 |
| WO | 2020014056 | A1 | 1/2020 |

OTHER PUBLICATIONS

Abridged Data Sheet, "DeepCover Secure Authenticator with 1-Wire SHA-256 and 512-Bit User EEPROM", Maxim Integrated Products, Inc. pp. 1-4; 42; Dec. 2012.

Data Sheet "DS28E15—1—Sire SHA-256 Secure Authenticator with 512-Bit User EEPROM"; IC-On-Line, Electronic Component Manufacturers, pp. 1-2; Aug. 2013.

U.S. Appl. No. 62/333,584, filed May 9, 2016 to Nicholas.

Extended European Search Report for application No. 21184879.1 dated Feb. 9, 2022.

* cited by examiner

METHODS AND STRUCTURE FOR CONFIRMING PROPER ASSEMBLY OF POWERED SURGICAL STAPLING SYSTEMS

CROSS REFERENCE TO RELATED APPLICATIONS

This application claims the benefit of U.S. Provisional Application Ser. No. 63/050,994, filed Jul. 13, 2020, the entire contents of which are incorporated by reference herein.

TECHNICAL FIELD

This disclosure relates to surgical stapling systems and, more particularly, to structures and methods for confirming proper assembly of powered surgical stapling systems.

BACKGROUND

Fasteners have traditionally been used to replace suturing when joining various body structures. Surgical stapling systems employed to apply these fasteners are generally designed to simultaneously cut and seal tissue to reduce the time and risks involved with surgical procedures. Surgical stapling systems that clamp, cut and/or staple tissue are well known in the art. Some surgical stapling systems are powered and include a handle assembly, an adapter assembly that couples to the handle assembly, and a reload or end effector assembly that couples to the adapter assembly. While the end effector assembly is typically a single use component, at least portions of the handle assembly and/or the adapter assembly require disassembly and cleaning for subsequent use.

SUMMARY

According to one aspect, a surgical stapling system includes an adapter assembly, a trocar assembly selectively attachable to the adapter assembly, a processor, and a memory including instructions stored thereon, which when executed by the processor, cause the surgical stapling system to move the trocar assembly relative to the adapter assembly and determine whether the trocar assembly is properly attached to the adapter assembly. Such determination is based on one or more of: an amount of force applied between the trocar assembly and the adapter assembly when the trocar assembly is moved relative to the adapter assembly, an amount of current detected in the surgical stapling system when the trocar assembly is moved relative to the adapter assembly, or an amount of time the trocar assembly moves relative to the adapter assembly without an indication that the amount of force is within a predetermined range.

In aspects, the surgical stapling system may further include a tip protector mounted to the trocar assembly. The tip protector may include a tip protector body and brace secured to the tip protector body. The brace may be positioned to engage a distal engagement protuberance of the outer housing of the adapter assembly to cause the amount of force between the trocar assembly and the adapter assembly to increase.

In aspects, the trocar assembly may include a trocar that is operatively coupled to a lead screw. The lead screw may be positioned to move the trocar relative to an outer housing of the adapter assembly to move the tip protector into engagement with the outer housing. A sensor may be positioned adjacent to the lead screw to detect an amount of movement of the lead screw relative to the outer housing. The sensor may be a strain gauge. The sensor may be configured to communicate a signal to the controller. The signal may be indicative of the amount of movement of the lead screw relative to the outer housing. The controller may be configured to determine the amount of force applied between the trocar assembly and the adapter assembly based on the signal. The controller may be configured to compare the amount of force applied between the trocar assembly and the adapter assembly to a threshold amount of force stored on the memory to determine if the trocar assembly and the adapter assembly are properly assembled.

In aspects, the instructions, when executed by the processor, may further cause the system to display an indication that the trocar assembly is not properly assembled to the adapter assembly or is properly assembled to the adapter assembly.

According to one aspect, the surgical stapling system includes an adapter assembly having an outer housing, a trocar assembly receivable within the outer housing of the adapter assembly and supporting a tip protector thereon, a processor, and a memory including instructions stored thereon. The instructions, when executed by the processor, cause the surgical stapling system to: move the tip protector relative to the outer housing, cause the tip protector to engage the outer housing of the adapter assembly, detect an amount of force applied between the tip protector and the adapter outer housing when the tip protector is moved relative to the outer housing, compare the amount of force detected to a threshold force stored on the memory, and if the amount of force detected is greater than the threshold force stored on the memory, selectively output an indication that the trocar assembly is properly secured to the adapter assembly.

In aspects, the instructions, when executed by the processor, may cause the surgical stapling system to: detect an amount of current in the surgical stapling system, compare the amount of current in the surgical stapling system to a threshold current indicative of a current spike, the threshold current stored on the memory, and if the amount of current in the surgical stapling system is at least equal to the threshold current, output an indication that that the trocar assembly is not properly secured to the adapter assembly.

In aspects, the instructions, when executed by the processor, may cause the surgical stapling system to measure the amount of time that the tip protector is instructed to move relative to the outer housing, compare the amount of time to a threshold time stored on the memory, and if the amount of time is at least equal to the threshold time, output an indication that the trocar assembly is not properly secured to the adapter assembly.

In aspects, the trocar assembly may include a trocar that is operatively coupled to a lead screw. The lead screw may be positioned to move the trocar relative to the adapter assembly to cause the tip protector to move relative to the outer housing. The surgical stapling system may include a sensor that is positioned adjacent to the lead screw to detect an amount of movement of the lead screw relative to the outer housing. The sensor may be a strain gauge.

In aspects, the surgical stapling system may further include a controller configured to determine the amount of force based on a signal from the sensor indicating the amount of movement of the lead screw relative to the outer housing.

According to another aspect, a method for determining if a trocar assembly of a surgical stapling system is properly attached to an adapter assembly of the surgical stapling system before attachment of an end effector to the trocar assembly is provided. The method includes moving the trocar assembly relative to the adapter assembly, selectively determining an amount of force applied between the trocar assembly and the adapter assembly when the trocar assembly is moved relative to the adapter assembly, selectively determining an amount of current in the surgical stapling system when the trocar assembly is moved relative to the adapter assembly, selectively determining an amount of time lapsed from when movement of the trocar assembly relative to the adapter assembly is initiated, and based on a determination of at least one of the amount of force determined, the amount of current determined, or the amount of time lapsed, selectively outputting an indication that the trocar assembly is properly secured to the adapter assembly or improperly secured to the adapter assembly.

According to still another aspect, a non-transitory storage medium that stores a program causing a processor to execute a method for determining if a trocar assembly of a surgical stapling system is properly attached to an adapter assembly of the surgical stapling system is provided. The method includes selectively determining an amount of force applied between the trocar assembly and the adapter assembly when the trocar assembly is moved relative to the adapter assembly, selectively determining an amount of current in the surgical stapling system when the trocar assembly is moved relative to the adapter assembly, selectively determining an amount of time lapsed from when movement of the trocar assembly relative to the adapter assembly is initiated, and based on a determination of at least one of the amount of force determined, the amount of current determined, or the amount of time lapsed, selectively outputting an indication that the trocar assembly is properly secured to the adapter assembly or improperly secured to the adapter assembly.

Other aspects, features, and advantages will be apparent from the description, the drawings, and the claims that follow.

BRIEF DESCRIPTION OF DRAWINGS

The accompanying drawings, which are incorporated in and constitute a part of this specification, illustrate aspects of the disclosure and, together with a general description of the disclosure given above and the detailed description given below, serve to explain the principles of this disclosure, wherein.

DETAILED DESCRIPTION

Aspects of the disclosed surgical stapling systems are described in detail with reference to the drawings, in which like reference numerals designate identical or corresponding elements in each of the several views. As commonly known, the term "clinician" refers to a doctor, a nurse, or any other care provider and may include support personnel. Additionally, the term "proximal" refers to the portion of structure that is closer to the clinician and the term "distal" refers to the portion of structure that is farther from the clinician. In addition, directional terms such as front, rear, upper, lower, top, bottom, and the like are used simply for convenience of description and are not intended to limit the disclosure attached hereto.

In the following description, well-known functions or constructions are not described in detail to avoid obscuring the present disclosure in unnecessary detail.

Further, although the surgical instrumentation described herein is provided in connection with a powered circular surgical stapling system for brevity, the disclosed surgical instrumentation can include any powered, manual, or robotically-controlled surgical instruments such as a clip applier, stitching device, energy-based device (e.g., a bipolar or monopolar forceps) or the like, and/or other surgical stapling systems such as a linear stapler, a transverse stapler, or an open stapler. For a detailed description of the structure and function of exemplary surgical stapling systems, one or more components of which may be included, or modified for use with the disclosed aspects, reference may be made to U.S. Pat. Nos. 9,713,470; 8,806,973; 8,256,656; 8,157,152; 8,070,033; 7,819,896; 7,770,774; 7,334,717; 7,128,253; 5,964,394; and 5,915,616, the entire contents of each of which are incorporated herein by reference.

Briefly, this disclosure details structure and methods for effectively relaying information/data from one or more sensors (e.g., strain gauges) in an adapter of a surgical stapling system to one or more controllers or processors, which may be part of (and/or remote from) the surgical stapling systems thereof (e.g., in a housing/handle assembly, robot arm, network, etc.) to accurately determine and/or analyze, for example, signals from the sensor(s). For instance, the sensors can be configured to sense force acting on the sensors and communicate signals to the processors so that the processors can determine, based on the signals, whether the trocar assembly of an adapter assembly is properly attached to the adapter assembly.

Figure 1:
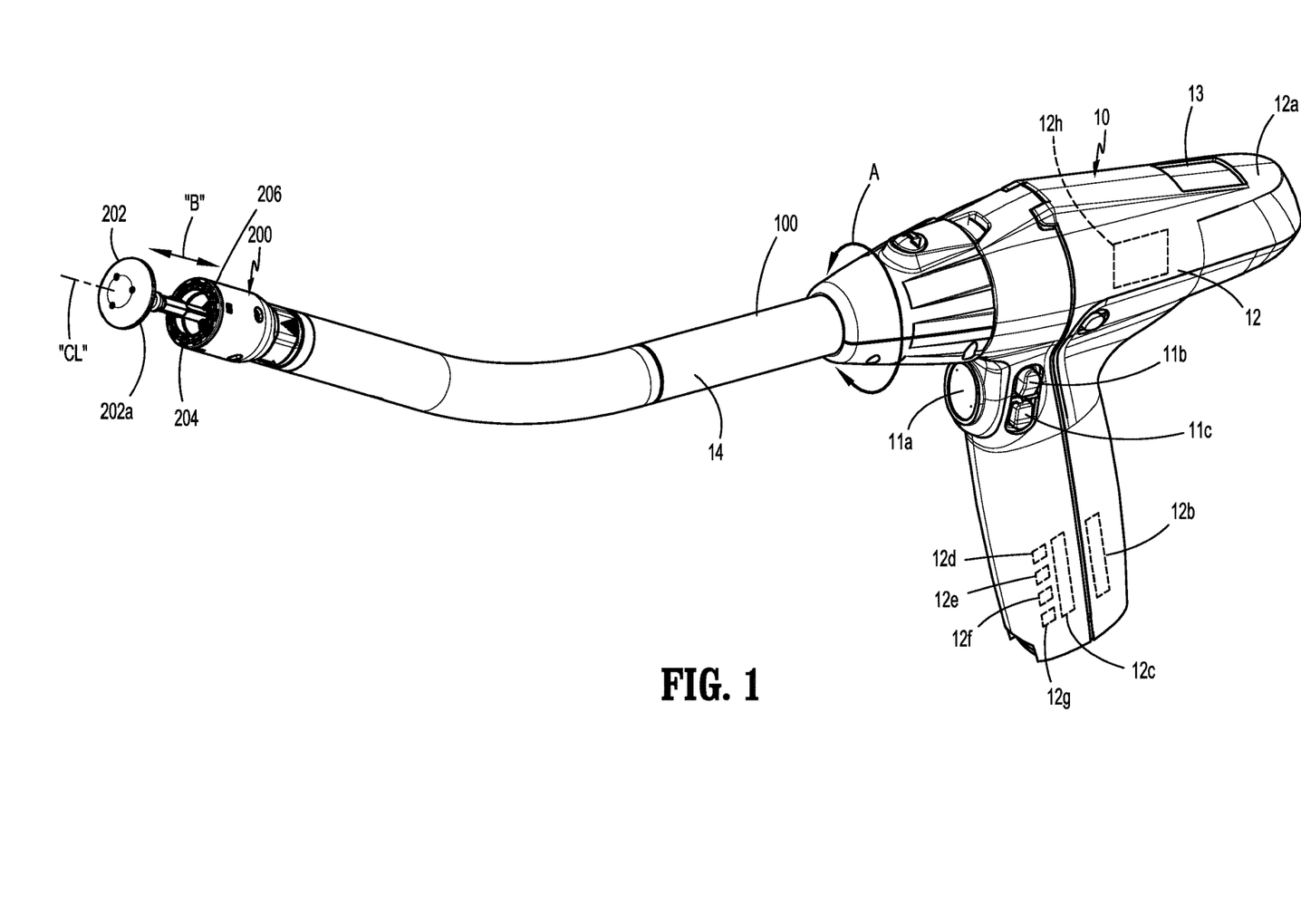
FIG. 1 is a perspective view of an illustrative surgical stapling system in accordance with the principles of this disclosure.

With reference to FIG. 1, a surgical stapling system 10 of this disclosure includes a housing assembly 12 (which may include one or more handles that may be manually actuatable to fire surgical stapling system 10) and an elongated shaft assembly 14 that is removably secured to housing assembly 12. Elongated shaft assembly 14 extends distally to housing assembly 12 and defines a centerline "CL" therealong. Elongated shaft assembly 14 includes an adapter assembly 100 having a proximal end portion removably secured to housing assembly 12. Elongated shaft assembly 14 further includes an end effector assembly 200 that is removably secured to a distal end portion of adapter assembly 100. End effector assembly 200 may be disposable and/or include one or more disposable components. End effector assembly 200 includes an anvil assembly 202 and a cartridge assembly 204 that houses a plurality of staples (not shown) in a reload or cartridge 206 thereof that may be selectively replaceable. Anvil assembly 202 includes an anvil 202a against which the plurality of staples is formed upon a firing of surgical stapling system 10.

Housing assembly 12 of surgical stapling system 10 includes a housing 12a configured for selective removable receipt of a rechargeable battery 12b. Battery 12b is configured to supply power to electrical components of surgical stapling system 10. Housing 12a supports a controller 12c (e.g., a circuit board) therein that is configured to control various operations of surgical stapling system 10, and which includes any number of electronic components such as memory 12d (which may include a storage device for storing data, and which may be a part of memory 12d or separate from memory 12d), a processor 12e, a network interface 12f, and/or other electrical circuitry such as (input/output modules, sensors, chips, wiring, etc.) 12g. As can be appreciated, memory 12d can include instructions stored thereon that are selectively executable by processor 12e, which cause the surgical stapling system or components thereof to effectuate one or more functions such as sensing, analyzing signals from sensors, and communicating signals to one or more components to effectuate one or more other functions such as preventing component movement or causing one more components to move or communicate with other components. Controller 12c may be electrically coupled to a local display device 13 (and/or a remote display device—not shown) for outputting information and/or data such as a condition of components of surgical stapling system 10. For instance, display device 13 can output an indication of whether adapter assembly 100 is properly operating and/or assembled.

Surgical stapling system 10 further includes a drive mechanism 12h configured to drive mechanical and/or electrical components such as rotatable shafts and/or gear components (not shown) within housing 12a in order to perform various operations of surgical stapling system 10. For instance, drive mechanism 12h may be operable to selectively move (e.g., rotate about) end effector 300 relative to the centerline "CL" of surgical stapling system 10, as indicated by arrows "A," to selectively move anvil assembly 202 relative to the cartridge assembly 204, as indicated by arrows "B," to selectively clamp tissue; and/or to fire surgical stapling system 10 for fastening and/or cutting the clamped tissue. Battery 12b, controller 12c, and/or drive mechanism 12h may be operably coupled to one or more actuators 11a, 11b, and 11c such as finger-actuated control buttons, rocker devices, and/or the like to effectuate various functions of surgical stapling system 10 such as those described above.

Figure 2:
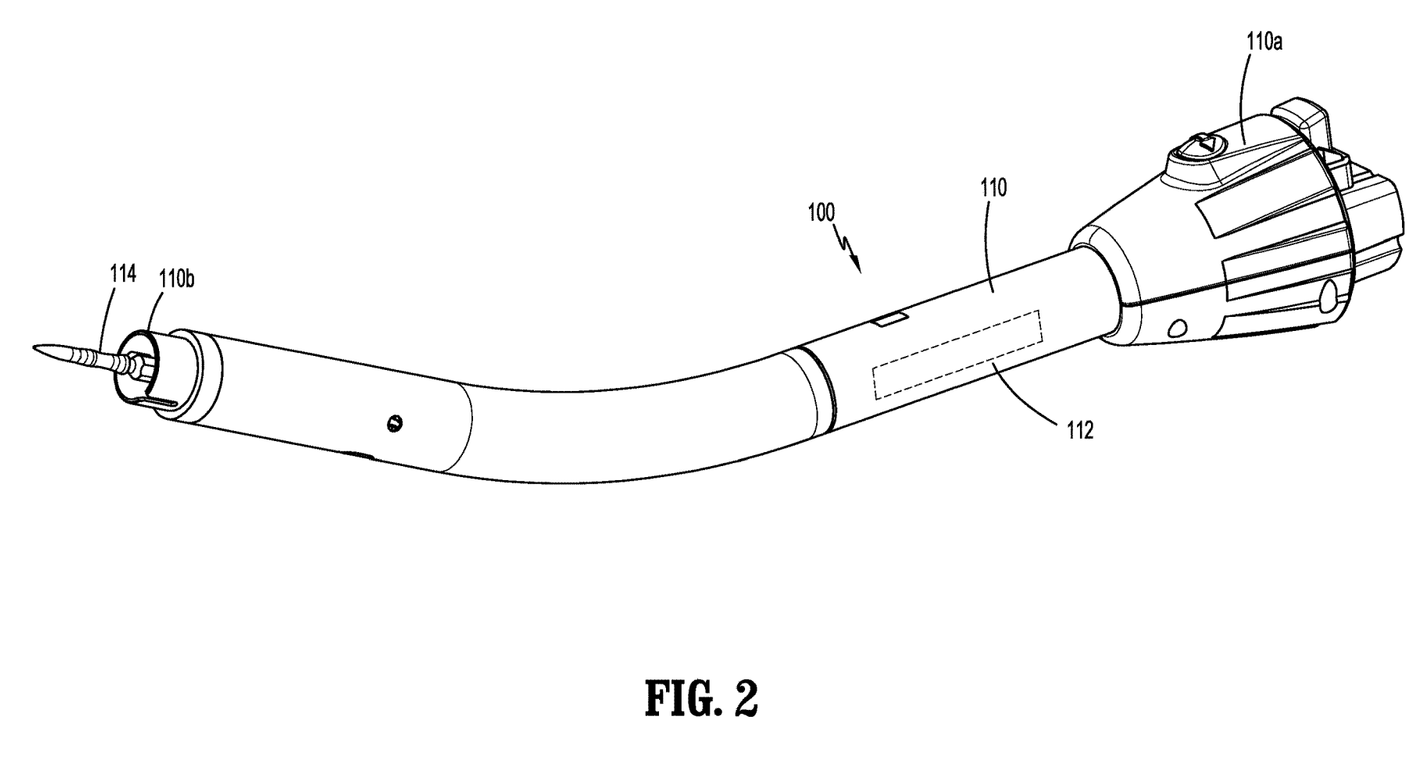
FIG. 2 is a perspective view of an adapter assembly of the surgical stapling system of FIG. 1.
Figure 7:
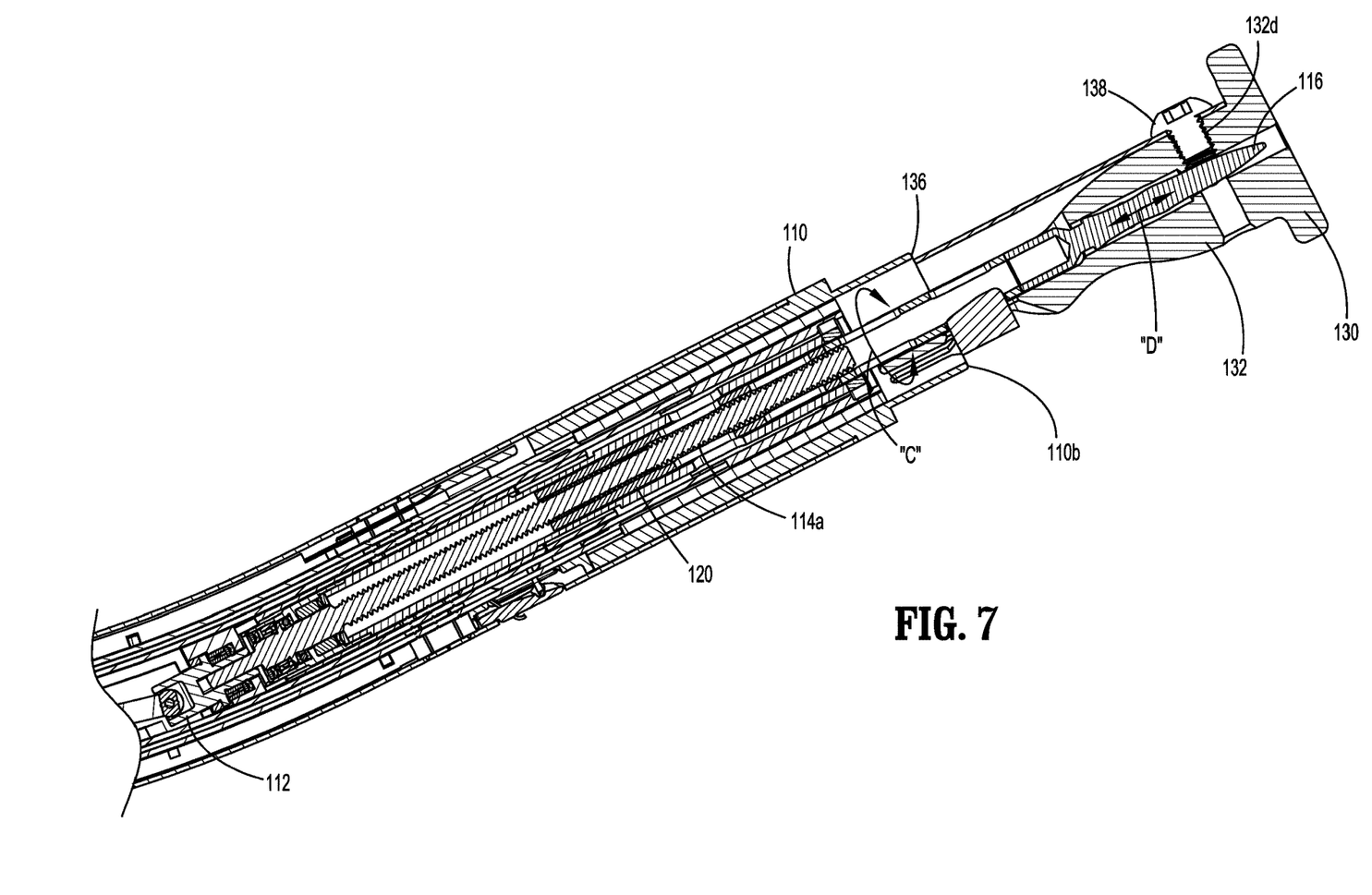

With reference to FIGS. 2 and 7, adapter assembly 100 of elongated shaft assembly 14 includes an outer housing 110 and supports a drive assembly 112 therein. Outer housing 110 extends from a proximal connector housing 110a to a distal engagement protuberance 110b. A distal end portion of drive assembly 112 operatively couples to proximal end portion of a trocar assembly 114, in particular to a lead screw 114a of trocar assembly 114 that is rotatable, as indicated by arrows "C," to translate a trocar 116 of trocar assembly 114, as indicated by arrows "D." Axial movement of trocar 116 causes anvil assembly 202 of end effector 200 to move relative to cartridge assembly 204, as indicated by arrows "B," when end effector 200 is coupled to adapter assembly 100 (FIG. 1). Adapter assembly 100 further includes one or more sensors 120, such as a strain gauge, positioned along lead screw 114a to detect a threshold force (e.g. 20 lbs.) within a predetermined range of movement (e.g., rotational and/or axial) of lead screw 114a relative to sensors 120 and/or other components of adapter assembly 100. Sensors 120 are disposed in electrical communication with controller 12c of housing assembly 12 of surgical stapling system 10.

Figures 3, 4:
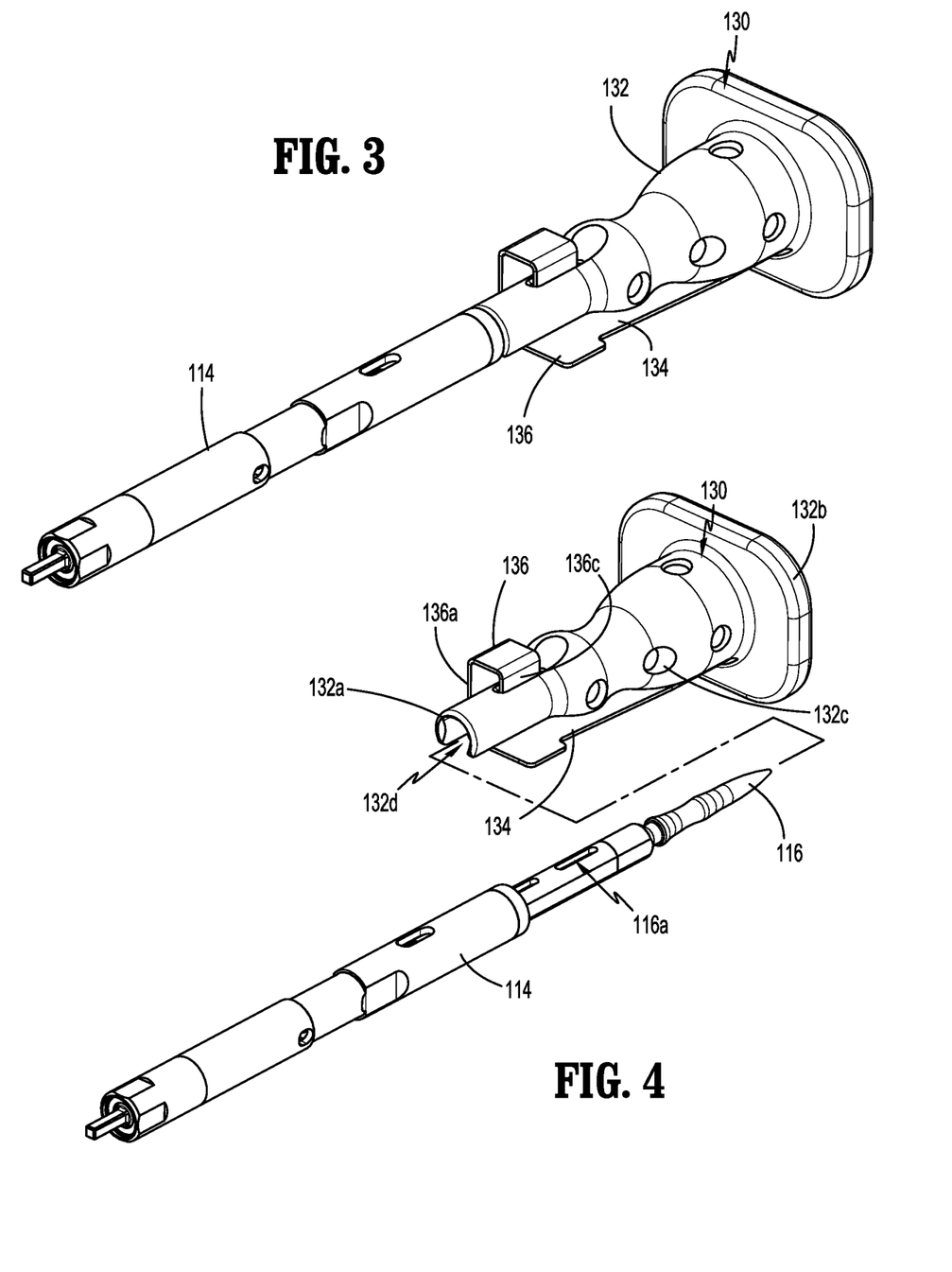
FIG. 3 is a perspective view of a trocar assembly of the adapter assembly of FIG. 2 with a tip protector shown supported thereon.
FIG. 4 is a perspective view, with parts separated, of the trocar assembly and tip protector of FIG. 3.
Figure 5:
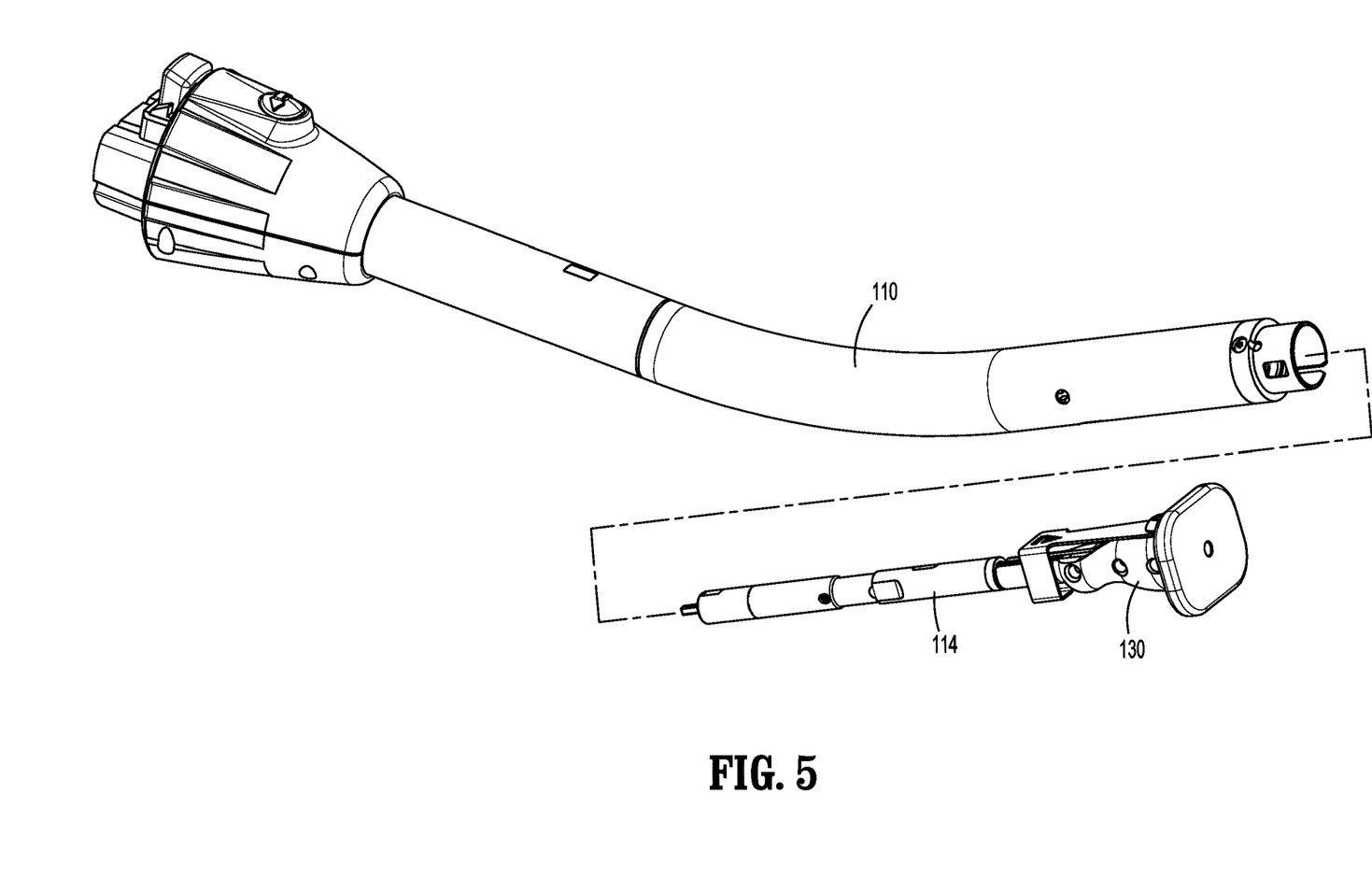
FIGS. 5-7 are progressive views illustrating the trocar assembly of FIG. 3 being removed from the adapter assembly of FIG. 2 and/or attached to the adapter assembly with the tip protector of FIG. 3 mounted thereon.
Figure 6:
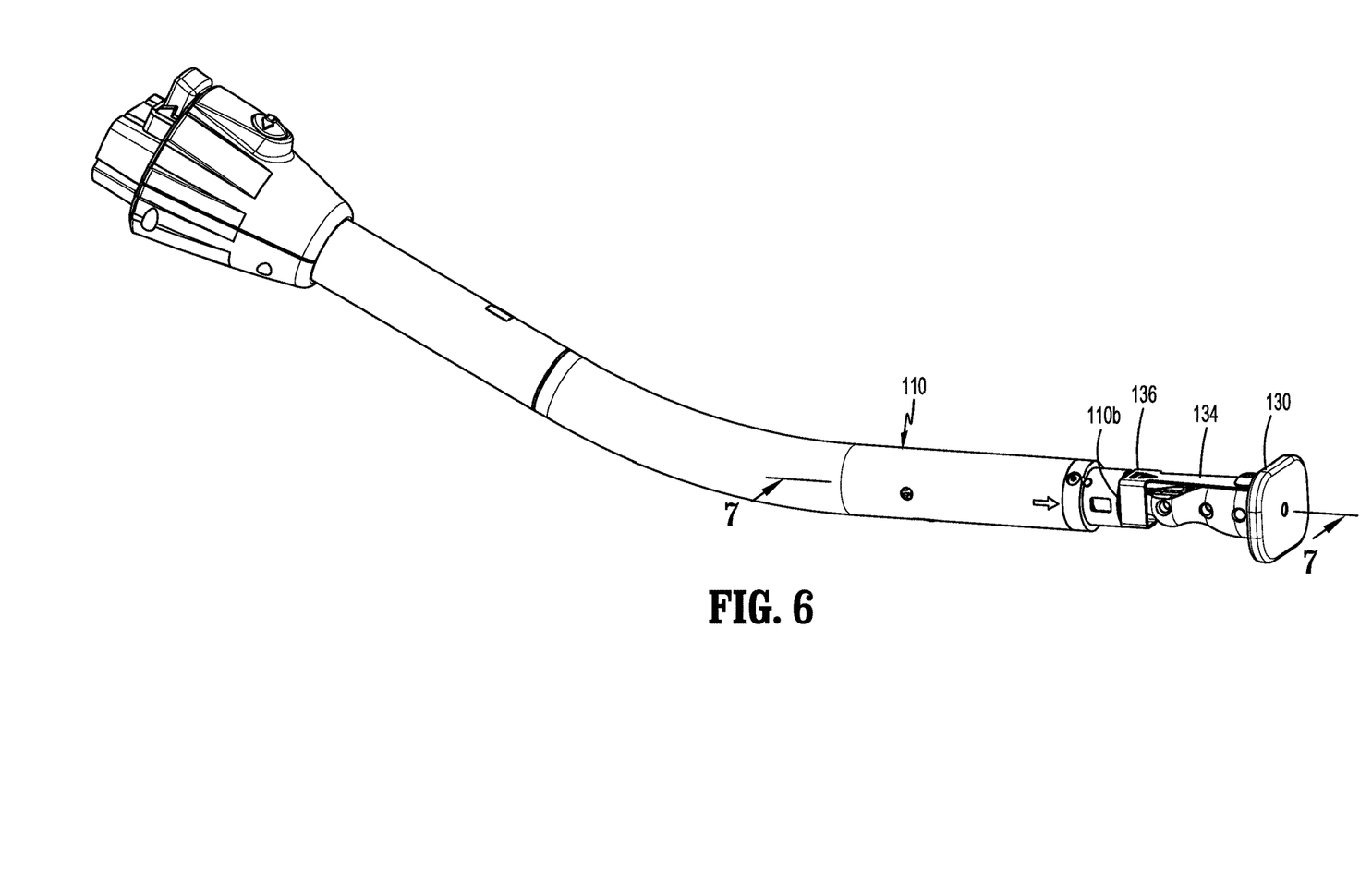

Referring to FIGS. 3-5, trocar assembly 114 of adapter assembly 200 is selectively removable from adapter assembly 200, for example, to effectuate a cleaning of adapter assembly 200. Trocar assembly 114 can further support a tip protector 130 thereon that protects trocar 116 when trocar assembly 114 is removed from adaptor assembly 100 and/or otherwise exposed without end effector 200 attached thereto. Tip protector 130 includes a tip protector body 132. Tip protector body 132 includes an arch 132a at a proximal end portion thereof and a flange 132b at a distal end portion thereof. Tip protector body 132 defines a plurality of apertures 132c therethrough and an arched channel 132d defined by arch 132a. Tip protector 130 further includes a brace 134 that extends proximally from a threaded distal opening 132d in tip protector body 132 to a contact base 136 (see FIG. 7). Threaded distal opening 132d receives a screw 138 to secure brace 134 to tip protector body 132. Contact base 136 includes transverse arms 136a, 136b and a clip 136c that depends from transverse arm 136a. Clip 136c extends through tip protector body 132 into the arched channel 132d. Clip 136c is positioned to engage a clip channel 116a defined in trocar assembly 114 for securing tip protector 130 to trocar assembly 114 as seen in FIG. 3. Arched channel 132c is positioned to receive trocar 116 therein so that trocar 116 can be retained within tip protector body 132 via frictionally and/or snap-fit arrangement.

With reference to FIGS. 1-8, when trocar assembly 114 is separated from adapter assembly 100, such as to effectuate a cleaning process of adapter assembly 100, re-attachment of trocar assembly 114 to adapter assembly 100 is required. To ensure trocar assembly 114 is properly attached, the surgical stapling system 10 includes software that analyzes signals from the sensors 120 and determines whether trocar assembly 114 is properly attached to adapter assembly 100. Once trocar assembly 114 is attached to adapter assembly 100 and adapter assembly 100 is secured to housing assembly 112, the assembly can be calibrated. The software includes instructions stored on memory 12d that, when executed by processor 12e to cause controller 12c to determine whether adapter assembly 100 is properly assembled and output a signal indicative of the propriety of the assembly, for example.

Briefly, sensor 120, detects forces greater than a threshold (e.g., 20 lbs.) within a specified range (e.g. distance) so that the software recognizes that the trocar assembly 114 was properly installed. If the sensor 120 does not detect a force greater than the threshold within the specified range of movement, lead screw 114a of trocar assembly 114 will bottom out, which can induce a current spike. The software can utilize the current spike for an indication that trocar assembly 114 was not properly assembled to adapter assembly 114. If neither event (current spike nor force threshold) occurs within a specified time limit, the system can be configured to indicate that the device was improperly assembled. The software can be configured to prevent the use of the device until a proper assembly verification is achieved.

Advantageously, such verification software prevents the reload from clamping and/or firing when the trocar assembly is not properly assembled with the adapter assembly. Indeed, the disclosed verification software prevents staples of the surgical stapling system from becoming under-crimped, prevents the surgical stapling system from effectuating incomplete tissue cutting, and/or prevents the reload from becoming locked onto the tissue.

Figure 8:
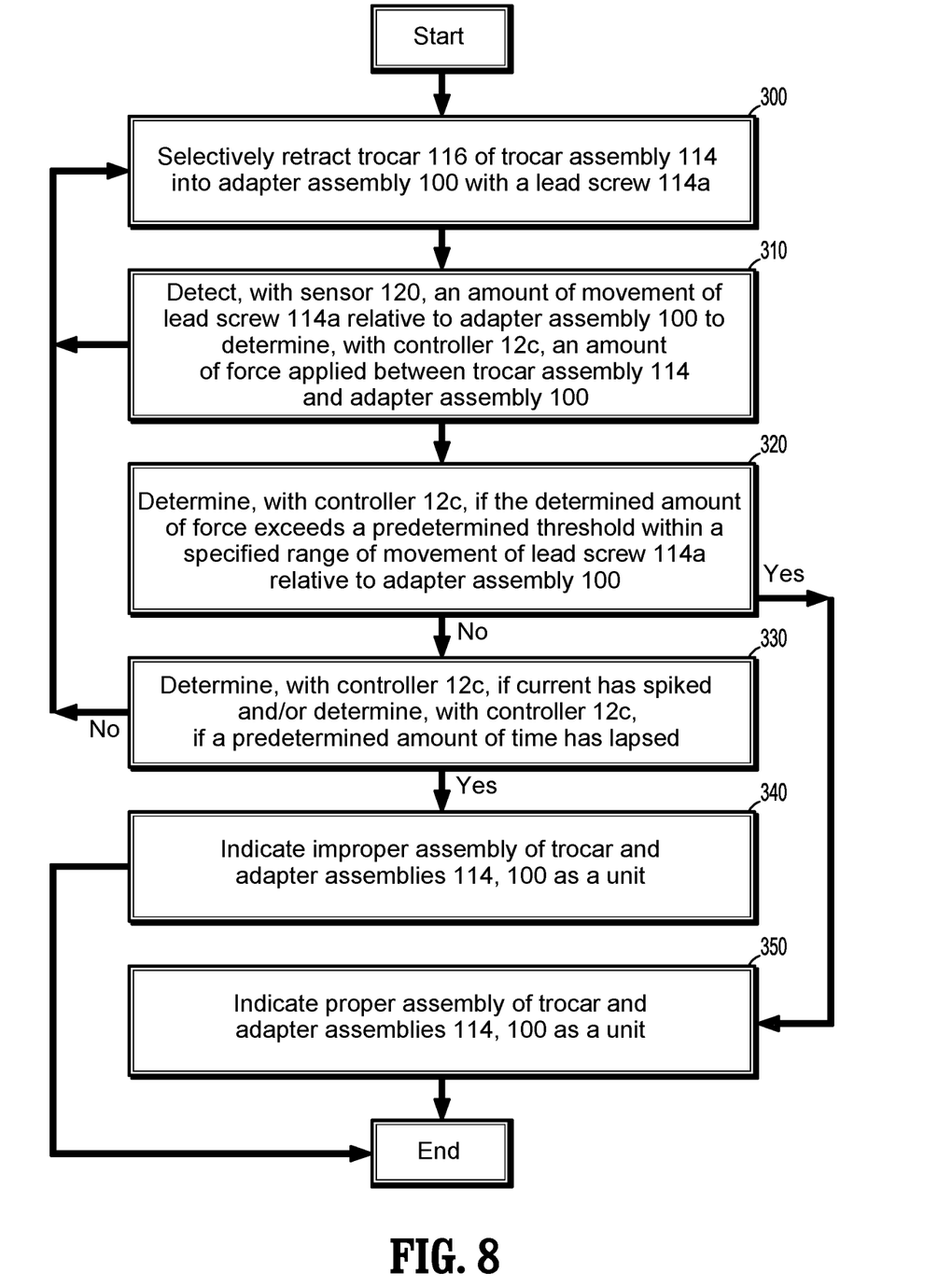
FIG. 8 is a flow chart illustrating a method for determining if the trocar assembly of FIG. 3 is properly attached to the adapter assembly of FIG. 2 when calibrating the surgical stapling system after being assembled with the tip protector of FIG. 3 supported thereon.

More specifically, as best illustrated in FIG. 8, in step 300, during calibration, trocar 116 of trocar assembly 114 can be retracted proximally upon an activation of drive assembly 112 that causes lead screw 114a to rotate. Continued proximal movement of trocar 116 causes contact base 136 of tip protector 130 to engage (e.g., contact) distal engagement protuberance 110b of outer housing 110 of adapter assembly 100. Such engagement will cause increase an amount of force being applied between trocar assembly 114 and adapter assembly 100 (e.g., via lead screw 114a).

In step 310, sensor 120, detects forces acting on lead screw 114a, which are counterforces opposing the engagement of distal engagement protuberance 110b of adapter assembly 100 and contact base 136 of tip protector 130. Such detected forces progressively increase as lead screw 114 is drawn in the proximal direction relative distal engagement protuberance 110b within a specified range of movement of the lead screw 114a (e.g. distance lead screw 114a travels relative to sensor 120). Sensor 120 transmits a signal (e.g., electrical such as a voltage and/or current signal) indicative of such distance travelled to, for example, controller 12c for controller 12c to analyze such signal.

In step 320, controller 12c determines, based on the signal from sensor 120, an amount of force being applied between trocar assembly 114 and adapter assembly 100. Controller 12c than compares such detected force to a predetermined threshold force stored, for example, on memory 12d (or a storage device thereof and/or in electrical communication therewith). If such detected force meets a predetermine threshold, which may be, for example 20 lbs. of force (although any suitable predetermined threshold force may be utilized), controller 12c can send a signal to indicate that assembly of trocar assembly 114 and adapter assembly 100 is proper. For instance, a controller 12c can send a signal that causes display 13 to output an indication that assembly is proper and/or that surgical stapling system 10 is ready for use or reuse as illustrated in step 350.

In step 330, controller 12c can determine, for example, from signals sent from a current sensor or timer (not shown) electrically coupled thereto, if there was an improper assembly. For instance, if lead screw 114a has bottomed out, a current spike (e.g., 8-10 amps) will occur in the system (and/or a predetermined amount of current will be detected). Alternatively, and/or additionally, if a predetermined amount of time has lapsed without an indication of proper assembly, controller 12c can determine that there was improper assembly. More particularly, if current reaches a predetermined threshold (or spike) and/or a predetermined amount of time lapses (e.g., 5-10 seconds) without an indication that there was a proper assembly of trocar assembly 114 and adapter assembly 100, controller 12c determines there was an improper assembly. In such instances, controller 12c can send a signal that causes display 13 to indicate that there was an improper assembly as illustrated in step 340. Alternatively, and/or additionally, controller 12c can send one or more signals that lockout and/or prevent surgical stapling system 10, or components thereof (e.g., end effector 200) from operating until surgical stapling system 10 is properly assembled.

Further, the various aspects disclosed herein may also be configured to work with robotic surgical systems and what is commonly referred to as "Telesurgery." Such systems employ various robotic elements to assist the clinician and allow remote operation (or partial remote operation) of surgical instrumentation. Various robotic arms, gears, cams, pulleys, electric and mechanical motors, etc. may be employed for this purpose and may be designed with a robotic surgical system to assist the clinician during the course of an operation or treatment. Such robotic systems may include remotely steerable systems, automatically flexible surgical systems, remotely flexible surgical systems, remotely articulating surgical systems, wireless surgical systems, modular or selectively configurable remotely operated surgical systems, etc.

The robotic surgical systems may be employed with one or more consoles that are next to the operating theater or located in a remote location. In this instance, one team of clinicians may prep the patient for surgery and configure the robotic surgical system with one or more of the instruments disclosed herein while another clinician (or group of clinicians) remotely controls the instruments via the robotic surgical system. As can be appreciated, a highly skilled clinician may perform multiple operations in multiple locations without leaving his/her remote console which can be both economically advantageous and a benefit to the patient or a series of patients. For a detailed description of exemplary medical work stations and/or components thereof, reference may be made to U.S. Patent Application Publication No. 2012/0116416, and PCT Application Publication No. WO2016/025132, the entire contents of each of which are incorporated by reference herein.

Moreover, the disclosed electronic structure such as the electronic assembly and/or controllers, can include any suitable electrical components for operating the disclosed surgical stapling systems or components thereof. Such electrical components can include, for example, one or more controllers and/or circuitry, which may include or be coupled to one or more printed circuit boards. As used herein, the term "controller" includes "processor," "digital processing device" and like terms, and are used to indicate a microprocessor or central processing unit (CPU). The CPU is the electronic circuitry within a computer that carries out the instructions of a computer program by performing the basic arithmetic, logical, control and input/output (I/O) operations specified by the instructions, and by way of non-limiting examples, include server computers. In some aspects, the controller includes an operating system configured to perform executable instructions. The operating system is, for example, software, including programs and data, which manages hardware of the disclosed surgical stapling systems and provides services for execution of applications for use with the disclosed surgical stapling systems. Those of skill in the art will recognize that suitable server operating systems include, by way of non-limiting examples, Free-BSD, OpenBSD, NetBSD®, Linux, Apple® Mac OS X Server®, Oracle® Solaris®, Windows Server®, and Novell® NetWare®. In some aspects, the operating system is provided by cloud computing.

In some aspects, the term "controller" may be used to indicate a device that controls the transfer of data from a computer or computing device to a peripheral or separate device and vice versa, and/or a mechanical and/or electro-mechanical device (e.g., a lever, knob, etc.) that mechanically operates and/or actuates a peripheral or separate device.

In aspects, the controller includes a storage and/or memory device. The storage and/or memory device is one or more physical systems used to store data or programs on a temporary or permanent basis. In some aspects, the controller includes volatile memory and requires power to maintain stored information. In various aspects, the controller includes non-volatile memory and retains stored information when it is not powered. In some aspects, the non-volatile memory includes flash memory. In certain aspects, the non-volatile memory includes dynamic random-access memory (DRAM). In some aspects, the non-volatile memory includes ferroelectric random-access memory (FRAM). In various aspects, the non-volatile memory includes phase-change random access memory (PRAM). In certain aspects, the controller is a storage device including, by way of non-limiting examples, CD-ROMs, DVDs, flash memory devices, magnetic disk drives, magnetic tapes drives, optical disk drives, and cloud computing based storage. In various aspects, the storage and/or memory device is a combination of devices such as those disclosed herein.

In some aspects, the controller includes a display to send visual information to a user. In various aspects, the display is a cathode ray tube (CRT). In various aspects, the display is a liquid crystal display (LCD). In certain aspects, the display is a thin film transistor liquid crystal display (TFT-LCD). In aspects, the display is an organic light emitting diode (OLED) display. In certain aspects, on OLED display is a passive-matrix OLED (PMOLED) or active-matrix OLED (AMOLED) display. In aspects, the display is a plasma display. In certain aspects, the display is a video projector. In various aspects, the display is interactive (e.g., having a touch screen or a sensor such as a camera, a 3D sensor, a LiDAR, a radar, etc.) that can detect user interactions/gestures/responses and the like. In some aspects, the display is a combination of devices such as those disclosed herein.

The controller may include or be coupled to a server and/or a network. As used herein, the term "server" includes "computer server," "central server," "main server," and like terms to indicate a computer or device on a network that manages the surgical stapling systems, components thereof, and/or resources thereof. As used herein, the term "network" can include any network technology including, for instance, a cellular data network, a wired network, a fiber optic network, a satellite network, and/or an IEEE 802.11a/b/g/n/ac wireless network, among others.

In various aspects, the controller can be coupled to a mesh network. As used herein, a "mesh network" is a network topology in which each node relays data for the network. All mesh nodes cooperate in the distribution of data in the network. It can be applied to both wired and wireless networks. Wireless mesh networks can be considered a type of "Wireless ad hoc" network. Thus, wireless mesh networks are closely related to Mobile ad hoc networks (MANETs). Although MANETs are not restricted to a specific mesh network topology, Wireless ad hoc networks or MANETs can take any form of network topology. Mesh networks can relay messages using either a flooding technique or a routing technique. With routing, the message is propagated along a path by hopping from node to node until it reaches its destination. To ensure that all its paths are available, the network must allow for continuous connections and must reconfigure itself around broken paths, using self-healing algorithms such as Shortest Path Bridging. Self-healing allows a routing-based network to operate when a node breaks down or when a connection becomes unreliable. As a result, the network is typically quite reliable, as there is often more than one path between a source and a destination in the network. This concept can also apply to wired networks and to software interaction. A mesh network whose nodes are all connected to each other is a fully connected network.

In some aspects, the controller may include one or more modules. As used herein, the term "module" and like terms are used to indicate a self-contained hardware component of the central server, which in turn includes software modules. In software, a module is a part of a program. Programs are composed of one or more independently developed modules that are not combined until the program is linked. A single module can contain one or several routines, or sections of programs that perform a particular task.

As used herein, the controller includes software modules for managing various aspects and functions of the disclosed surgical stapling systems or components thereof.

The disclosed surgical stapling systems may also utilize one or more controllers to receive various information and transform the received information to generate an output. The controller may include any type of computing device, computational circuit, or any type of processor or processing circuit capable of executing a series of instructions that are stored in memory. The controller may include multiple processors and/or multicore central processing units (CPUs) and may include any type of processor, such as a microprocessor, digital signal processor, microcontroller, programmable logic device (PLD), field programmable gate array (FPGA), or the like. The controller may also include a memory to store data and/or instructions that, when executed by the one or more processors, cause the one or more processors to perform one or more methods and/or algorithms.

Any of the herein described methods, programs, algorithms, or codes may be converted to, or expressed in, a programming language or computer program. The terms "programming language" and "computer program," as used herein, each include any language used to specify instructions to a computer, and include (but is not limited to) the following languages and their derivatives: Assembler, Basic, Batch files, BCPL, C, C+, C++, Delphi, Fortran, Java, JavaScript, machine code, operating system command languages, Pascal, Perl, PL1, scripting languages, Visual Basic, metalanguages which themselves specify programs, and all first, second, third, fourth, fifth, or further generation computer languages. Also included are database and other data schemas, and any other meta-languages. No distinction is made between languages which are interpreted, compiled, or use both compiled and interpreted approaches. No distinction is made between compiled and source versions of a program. Thus, reference to a program, where the programming language could exist in more than one state (such as source, compiled, object, or linked) is a reference to any and all such states. Reference to a program may encompass the actual instructions and/or the intent of those instructions.

As can be appreciated, securement of any of the components of the disclosed systems can be effectuated using known securement techniques such welding, crimping, gluing, fastening, etc. Also, any of the disclosed structure can include any suitable conductive material (e.g., metallic), semi-conductive material (e.g., silicone), and/or non-conductive/insulative material (e.g., plastic).

Persons skilled in the art will understand that the structures and methods specifically described herein and illustrated in the accompanying figures are non-limiting exemplary aspects, and that the description, disclosure, and figures should be construed merely as exemplary of particular aspects. It is to be understood, therefore, that this disclosure is not limited to the precise aspects described, and that various other changes and modifications may be effectuated by one skilled in the art without departing from the scope or spirit of the disclosure. Additionally, it is envisioned that the elements and features illustrated or described in connection with one exemplary aspect may be combined with the elements and features of another without departing from the scope of this disclosure, and that such modifications and variations are also intended to be included within the scope of this disclosure. Indeed, any combination of any of the disclosed elements and features is within the scope of this disclosure. Accordingly, the subject matter of this disclosure is not to be limited by what has been particularly shown and described.

What is claimed is:

1. A surgical stapling system, comprising:
an adapter assembly;
a trocar assembly selectively attachable to the adapter assembly;
a processor;
a memory including instructions stored thereon, which when executed by the processor, cause the surgical stapling system to:
move the trocar assembly relative to the adapter assembly; and
determine whether the trocar assembly is properly attached to the adapter assembly based on at least one of:
an amount of force applied between the trocar assembly and the adapter assembly when the trocar assembly is moved relative to the adapter assembly;
an amount of current detected in the surgical stapling system when the trocar assembly is moved relative to the adapter assembly; or
an amount of time the trocar assembly moves relative to the adapter assembly without an indication that the amount of force is in a predetermined range.

2. The surgical stapling system of claim 1, further comprising a tip protector mounted to the trocar assembly.

3. The surgical stapling system of claim 2, wherein the trocar assembly includes a trocar that is operatively coupled to a lead screw, the lead screw positioned to move the trocar relative to an outer housing of the adapter assembly to move the tip protector into engagement with the outer housing.

4. The surgical stapling system of claim 3, further comprising a sensor that is positioned adjacent to the lead screw to detect an amount of movement of the lead screw relative to the outer housing.

5. The surgical stapling system of claim 4, wherein the sensor is a strain gauge.

6. The surgical stapling system of claim 4, wherein the sensor is configured to communicate a signal to the controller, the signal indicative of the amount of movement of the lead screw relative to the outer housing.

7. The surgical stapling system of claim 6, wherein the controller is configured to determine the amount of force applied between the trocar assembly and the adapter assembly based on the signal.

8. The surgical stapling system of claim 7, wherein the controller is configured to compare the amount of force applied between the trocar assembly and the adapter assembly to a threshold amount of force stored on the memory to determine if the trocar assembly and the adapter assembly are properly assembled.

9. The surgical stapling system of claim 8, wherein the instructions, when executed by the processor, further cause the system to display an indication that the trocar assembly is not properly assembled to the adapter assembly or is properly assembled to the adapter assembly.

10. The surgical stapling system of claim 2, wherein the tip protector includes a tip protector body and brace secured to the tip protector body, the brace positioned to engage a distal engagement protuberance of the outer housing of the adapter assembly to cause the amount of force between the trocar assembly and the adapter assembly to increase.

11. A surgical stapling system, comprising:
an adapter assembly having an outer housing;
a trocar assembly receivable within the outer housing of the adapter assembly and supporting a tip protector thereon;
a processor; and
a memory including instructions stored thereon, which when executed by the processor, cause the surgical stapling system to:
move the tip protector relative to the outer housing;
cause the tip protector to engage the outer housing of the adapter assembly;
detect an amount of force applied between the tip protector and the adapter outer housing when the tip protector is moved relative to the outer housing;
compare the amount of force detected to a threshold force stored on the memory; and
if the amount of force detected is greater than the threshold force stored on the memory, selectively output an indication that the trocar assembly is properly secured to the adapter assembly.

12. The surgical stapling system according to claim 11, wherein the instructions, when executed by the processor, cause the surgical stapling system to:
detect an amount of current in the surgical stapling system;
compare the amount of current in the surgical stapling system to a threshold current indicative of a current spike, the threshold current stored on the memory; and
if the amount of current in the surgical stapling system is at least equal to the threshold current, output an indication that that the trocar assembly is not properly secured to the adapter assembly.

13. The surgical stapling system according to claim 12, wherein the instructions, when executed by the processor, cause the surgical stapling system to measure the amount of time that the tip protector is instructed to move relative to the outer housing;
compare the amount of time to a threshold time stored on the memory; and
if the amount of time is at least equal to the threshold time, output an indication that the trocar assembly is not properly secured to the adapter assembly.

14. The surgical stapling system of claim 11, wherein the trocar assembly includes a trocar that is operatively coupled to a lead screw, the lead screw positioned to move the trocar relative to the adapter assembly to cause the tip protector to move relative to the outer housing.

15. The surgical stapling system of claim 14, further comprising a sensor that is positioned adjacent to the lead screw to detect an amount of movement of the lead screw relative to the outer housing.

16. The surgical stapling system of claim 15, wherein the sensor is a strain gauge.

17. The surgical stapling system of claim 15, further comprising a controller configured to determine the amount of force based on a signal from the sensor indicating the amount of movement of the lead screw relative to the outer housing.

18. A method for determining if a trocar assembly of a surgical stapling system is properly attached to an adapter assembly of the surgical stapling system before attachment of an end effector to the trocar assembly, the method comprising:
moving the trocar assembly relative to the adapter assembly;

selectively determining an amount of force applied between the trocar assembly and the adapter assembly when the trocar assembly is moved relative to the adapter assembly;

selectively determining an amount of current in the surgical stapling system when the trocar assembly is moved relative to the adapter assembly;

selectively determining an amount of time lapsed from when movement of the trocar assembly relative to the adapter assembly is initiated; and based on a determination of at least one of the amount of force determined, the amount of current determined, or the amount of time lapsed, selectively outputting an indication that the trocar assembly is properly secured to the adapter assembly or improperly secured to the adapter assembly.

19. A non-transitory storage medium that stores a program causing a processor to execute a method for determining if a trocar assembly of a surgical stapling system is properly attached to an adapter assembly of the surgical stapling system, the method comprising:

selectively determining an amount of force applied between the trocar assembly and the adapter assembly when the trocar assembly is moved relative to the adapter assembly;

selectively determining an amount of current in the surgical stapling system when the trocar assembly is moved relative to the adapter assembly;

selectively determining an amount of time lapsed from when movement of the trocar assembly relative to the adapter assembly is initiated; and based on a determination of at least one of the amount of force determined, the amount of current determined, or the amount of time lapsed, selectively outputting an indication that the trocar assembly is properly secured to the adapter assembly or improperly secured to the adapter assembly.

* * * * *